(12) United States Patent
Liao et al.

(10) Patent No.: US 6,884,621 B2
(45) Date of Patent: Apr. 26, 2005

(54) METHOD AND CARRIER FOR CULTURING MULTI-LAYER TISSUE IN VITRO

(75) Inventors: Chun-Jen Liao, Hsinchu (TW); Yu-Ju Lin, Taipei (TW); Chin-Fu Chen, Taipei (TW)

(73) Assignee: Industrial Technology Research Institute, Hsiu Chu Hsien (TW)

( * ) Notice: Subject to any disclaimer, the term of this patent is extended or adjusted under 35 U.S.C. 154(b) by 0 days.

(21) Appl. No.: 10/620,339

(22) Filed: Jul. 17, 2003

(65) Prior Publication Data

US 2004/0121459 A1 Jun. 24, 2004

(30) Foreign Application Priority Data

Dec. 23, 2002 (TW) ........................................ 91137060 A

(51) Int. Cl.⁷ ................................................. C13N 5/08
(52) U.S. Cl. ........................................ 435/366; 435/395
(58) Field of Search ................................. 435/395, 366

(56) References Cited

U.S. PATENT DOCUMENTS

2002/0151968 A1 * 10/2002 Zilla et al. ................. 623/1.39

* cited by examiner

*Primary Examiner*—James Ketter
(74) *Attorney, Agent, or Firm*—Bacon & Thomas PLLC

(57) ABSTRACT

The present invention provides method and carrier for culturing multi-layered tissue in vitro, wherein few amounts of tissue blocks and cells are positioned within a porous multi-layer carrier consisting of a cavity structure. By taking advantage of the structure of the carrier, tissue blocks and cells are separated into different layers according to their sizes, and incubated in vitro to reconstruct a multi-layered tissue for tissue repair.

19 Claims, 5 Drawing Sheets

METHOD AND CARRIER FOR CULTURING MULTI-LAYER TISSUE IN VITRO

BACKGROUND OF THE INVENTION

1. Field of the Invention

The present invention relates to a novel method for culturing multi-layered tissues in vitro, wherein tissues and cells, by taking advantage of their disparity in volume, are to be distributed into different layers of a specific multi-layer porous carrier. When cultured in vitro, the tissues and cells grown in different layers of said carrier are to reconstruct a multi-layer tissue, so as to overcome the current technical bottleneck caused by the unavailability in culturing multi-layered tissues in vitro.

2. Description of the Prior Art

Due to the anticipated arrival of an aged society and an increasing number of people suffering from work or sports-related injuries, pathological changes on articular cartilage that causes painful reactions are clinical symptoms that cannot be overlooked. The articular cartilage lesions are classified into two groups according to their severity: partial thickness defect and full thickness defect. Partial thickness defect is the injury or erosion on the cartilage tissue of articular surface that does not reach the subchondral bone. Full thickness defect is the injury or erosion on the cartilage tissue that penetrates the subchondral bone. With the advancement in surgery operation and arthroscopy, partial thickness defect of articular cartilage lesions can be treated or its symptom can be relieved by surgery and arthroscopic methods such as abrasion arthroplasty, debridement and lavage, high tibial osteotomy, microfracturing, and drilling. However, general arthroscopy cannot cure full thickness defect where the damaged area is much wider and/or deeper than that of partial thickness defect. As a result, patients are faced with the only choice of undergoing both joint excision and replacement with an artificial joint to relieve pain and regain function of joints. It is estimated that over 150,000 knee replacement operations caused by full thickness defect are performed annually in the U.S., and the number of such operations is rising year after year. Because artificial joints are expensive, medical costs for hospitalization and surgery are high. Furthermore, because artificial joints are made of metals that last only about 10 to 20 years after being transplanted into human bodies, young patients must suffer from the pain of going through another surgical procedure in the future, while older patients, who, more often than not, are unable to go through another surgery, become handicapped and walking impaired, placing heavy burdens on both families and society. Therefore, there is a great need for the development of a technique for treating full-thickness defects.

In 1995, a Hungarian surgeon developed a technique for autologous implantation called Mosaic Plasty Procedure. Relying on arthroscopy, Mosaic Plasty Procedure is performed with a tube chisel that harvests a cylindrical plug of healthy cartilage and its subjacent subchondral bone from the patient's non-weight-bearing surface at the joints. Next, the damaged site is drilled with a tube chisel to make a hole of the same diameter as that of the cylindrical plug. Then, the cylindrical plug previously harvested from healthy cartilage is to be inserted into the hole of the damaged site. The procedures may be repeated several times when the damaged area is wide. By performing this technique, a new articular surface at damage site is formed. Because the mosaic appearance of new articular surface after surgery, the technique is termed Mosaic Plasty Procedure. Such technique has the merits of using patients' own tissues for transplantation, and thereby avoids immunogenic problems caused by using allograft or xenograft. Furthermore, the cylindrical plug is composed of biphasic joint, which contains cartilage and subjacent subchondral bone. After transplantation, peripheral bone tissue will grow into the spongy bone tissue of subchondral bone at the site of lesion. Such growth contributes to fixation of the transplant and reduces the problems caused by either suture fixation or transplant loosening. However, the autologous cartilage for transplantation is usually harvested from the non-weight-bearing surface of patients' joints, where the available area and volume are limited, and hence treating larger damaged area becomes unfeasible. Accordingly, the bottleneck in current technique is in the development of in vitro culturing technology to amplify the volume of autologous biphasic joint while maintaining the original characteristics of cartilage tissue.

The tissue engineering technique nowadays is limited to culturing single tissue, while in clinical application, tissues to be filled or restored are often composite tissues. For example, the human articular surface is a typical biphasic composite tissue. Current tissue engineering-related technique is mainly to utilize patients' own cells in cooperation with different porous carriers to reconstruct, in vitro or in vivo, the original framework of tissues by taking advantage of the three-dimensional structures of porous carriers. Generally speaking, such technique can only be used for culturing homogenous single tissues but not multi-layer tissues. Because the diameter of cells is smaller than that of the pore of porous carrier, when seeding two different cells in porous carrier, cells would flow around the carrier and mix-up but fail to grow in an orderly pattern into a multi-layer tissue. The present related technique is to grow and proliferate chondrocytes and osteocytes separately in vitro, followed by seeding cells so as to attach and incubate within two individual porous substrates to grow into tissues, and finally combine two tissues to obtain a multi-layer tissue by fusing their interfaces. This approach is time-consuming and a more practical technique is still under development.

SUMMARY OF THE INVENTION

To correct the drawbacks in the prior arts, the main object of the present invention is to provide a novel and effective method to culture multi-layered tissue in vitro that comprises the following steps: providing a porous multi-layer carrier having hollow cavity; placing tissue blocks within the hollow cavity of the foregoing carrier; seeding cells into the foregoing carrier; and incubating the tissue blocks and cells within the foregoing carrier in a culture medium.

The foregoing tissue blocks are created through the procedures of cutting into pieces and enzyme digestion so as to dissolve partial cells from tissue blocks. The diameter of tissue blocks is preferably from 500 to 1000 μm. The foregoing tissue blocks can be granulated carriers attached with cells or cell aggregates.

The foregoing cell, according to the present invention, is any preparation of living tissue, including primary tissue explants and preparations thereof, an isolated cell, and a cell line.

Another object of the present invention is to provide a multi-layer porous carrier for culturing multi-layered tissue, comprising at least one hollow cavity that is for receiving tissue blocks and is surrounded by a wall of porous substrate, and a porous structure which locates under the hollow cavity and provides for cell attachment.

The pore diameter of the foregoing multi-layer porous carrier ranges preferably from 50 to 500 µm. The foregoing multi-layer porous carrier is preferably made of any bioabsorbable polymer material. The term "Bioresorbable" refers to the ability of a material to be resorbed in vivo. The absorbable polymer material can is selected from the group consisting of polyglycolic acid (PGA), polylactic acid (PLA), poly(lactic-co-glycolic) acid (PLGA), polyanhydride, polycapralactone (PCL), polydioxanone and polyorthoester.

The bioabsorbable polymer material also can be composite material that comprises the forgoing absorbable polymer material and other materials. The foregoing other materials can be selected from the group consisting of hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), calcium pyrophosphate (CPP), collagen, gelatin, hyaluronic acid, chitin, and poly(ethylene glycol).

Another object of the present invention is to provide a multi-layer implant fabricated by the foregoing culturing method. The foregoing multi-layer implant is preferably a bone implant.

BRIEF DESCRIPTION OF THE DRAWINGS

These and other features, aspects and advantages of the present invention will become better understood with regard to the following description, appended claims and accompanying drawings that are provided only for further elaboration without limiting or restricting the present invention, where:

DETAILED DESCRIPTION OF THE INVENTION

Figure 1:
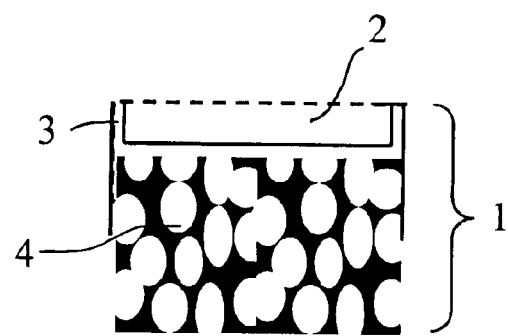
FIG. 1 is the schematic diagram of porous multi-layer carrier of the present invention.

As shown in FIG. 1, the multi-layer porous carrier 1 of the present invention comprises an upper hollow cavity 2 for receiving tissue blocks which is surrounded by a wall of porous substrate 3; and a porous structure 4, located under the hollow cavity 2, which is provided for cell attachment. The porous structure 4 is made of composite materials that combine bioabsorbable polymer and bioceramics so as to simulate the subchondral bone.

The culturing method of the present invention is performed by the multi-layer porous carrier 1 using the following procedure: Cartilage tissues are injected into said hollow cavity 2. Cartilage tissues would remain inside the hollow cavity 2 due to the fact that the diameter of the porous substrate 3 is smaller than that of the cartilage tissues. Then, the autologous bone marrow mesenchymal cells, which has been previously cultured and proliferated in vitro, are distributed evenly into the multi-layer porous carrier 1, and the cells are allowed to attach to the carriers and grow in vivo or in vitro. Due to the innate proliferation and fusion abilities, cartilage tissues in hollow cavity would grow and extend into the lower bone-like porous structure 4, while the mesenchymal cells would attach to the composite polymeric/ceramic porous structure 4 and grow into a layer of cells. Using the method described in the present invention, one can grow the foregoing tissues and cells into a two-layered cartilage, similar to the cartilage harvested by Mosaic Plasty Procedure. In the future, by taking only few amounts of cartilage tissue and bone marrow from the patient, and incubating subsequently with the invented multi-layer porous carrier in a culture medium under conditions promoting cell growth, one is able to grow large amounts of tissues that can be used as implants in transplantation surgery to treat symptoms attributed to full thickness defect typified by damaged areas that are quite wide and deep.

Below describes several examples to explicate how the invention is performed and its efficacy. However, the scope of the present invention is not limited to what is being described but is according to the appended claims. Individuals who are skilled in the art, without deviating from the scope and sprit of present invention, may perform appropriate modifications and adjustments.

Preferred Embodiments

EXAMPLE 1

Materials for Making Multi-Layered Porous Carrier

In this example, a mixture of hydroxyapatite (HAP) and poly (lactic-co-glycolic) acid (PLGA), which is prepared by ring open polymerization and has a molecular weight of 580,000 as determined by gel permeation chromatography, is utilized as bioabsorbable materials. Also, NaCl particle with diameter at about 250 µm is added to produce apertures. The organic solvent for dissolving polymeric particles is acetone.

EXAMPLE 2

Method for Preparing Multi-Layer Porous Carrier

Preparation of the Wall of Porous Substrate Surrounding the Upper Hollow Cavity is Performed According to the Procedure Below:

Dissolve 2 g of PLGA polymer particles and 8 g of NaCl evenly in 40 mL acetone to make the weight ratio of PLGA to NaCl to be at 20% to 80%. Next, pour the PLGA and NaCl mixture into a square teflon mold having 10 cm width and 0.5 cm height, and place the mixture and the mold in a laminar flow to evaporate organic solvent. The NaCl particle-contained PLGA membrane (with 0.8 mm thickness) is taken out from the mold and trimmed into a round-shaped flake of 7 mm in diameter and a rectangular sheet having 22 mm length and 5 mm width.

Preparation of the Lower Porous Structure is Performed According to the Procedure Below:

Dissolve PLGA blocks evenly in 40 mL acetone, followed by adding HAP so as to make a polymeric PLGA/HAP mixture with the weight ratio of PLGA to HAP mixture being at 50% to 50%. Pour the thick PLGA/HAP mixture into a square teflon mold and placed the mixture and the mold in a laminar flow to evaporate organic solvent. Next, crush the block-shaped PLGA/HAP polymer material in the pulverizer and sift the material through a sieve having 40 to 60 meshes to obtain the polymer particles with diameters ranging from 250 to 440 $\mu$m. The resulting PLGA/HAP composite particles are dry mixed with NaCl particles, letting the weight ratio of composite to NaCl to be at 20% to 80%.

Fabrication of Multi-Layer Porous Carrier:

Place the foregoing round flake of NaCl particle-contained PLGA into a round-shaped teflon filtering flask having 7 mm in diameter with the lower end thereof connected to an exhaust device, and surround the flask peripherally by the foregoing rectangular PLGA sheet to make a round fillister. Fill the round fillister with 0.07 g of NaCl particles and then tightly compress. At this time pour the organic solvent acetone into the mixture of particles, which are dipped in acetone. Next, turn on the exhaust valve to produce a negative pressure downward that extracts superfluous solvent. This extraction enables the dissolved polymer particles to adhere to one another. Then, pour deionized water onto the top of the filter. At the same time turn on the exhaust valve to allow large quantity of water to flow through the material. At this point, the polymer particles are dialyzed and solidified, and the sodium chloride particles in the interior are washed out by water. Next, take out the solidified polymer particles from the filter to be placed into a large beaker containing deionized water. While under normal room temperature, the water shall be changed every six hours. Furthermore, immerse the solidified polymer particles in water and wash the particles by water for a day by way of spinning to wash out the remaining solvent and salt particles. Next, heat and dry the solidified polymer particles in a vacuum oven at 50° C. for a day to form a multi-layered porous carrier having an upper hollow cavity. Immerse the multi-layered porous carrier in 75% alcohol for 6 hours, followed by replacing the alcohol with a substantial amount of sterilized phosphate buffered saline.

Figure 2:
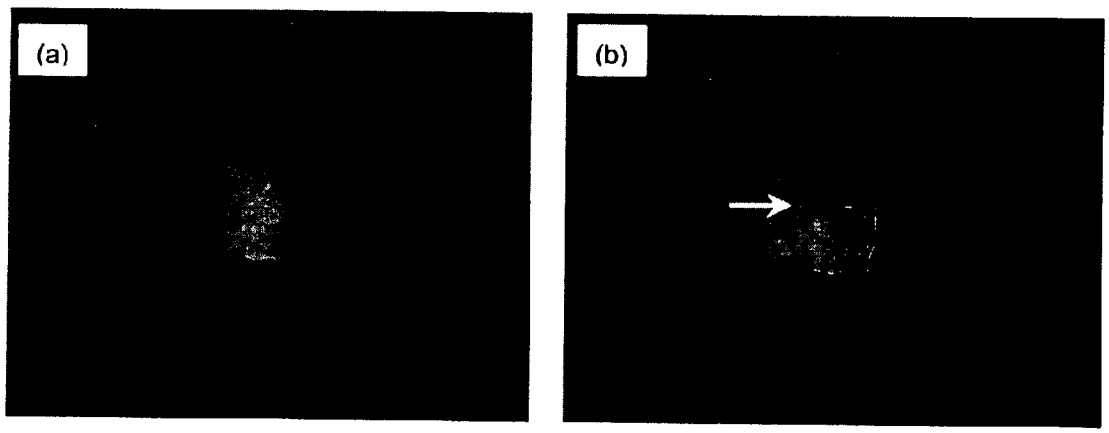
FIG. 2(a) shows the appearance of porous multi-layer carrier of the present invention.
FIG. 2(b) shows a cross-sectional view of porous multi-layer carrier of the present invention.

Results:

The appearance of multi-layered porous carrier prepared by the invented method is shown in FIG. 2(a). Its cross-sectional structure, as shown in FIG. 2(b), shows a hollow cavity being surrounded by a 1 mm thick wall as indicated by the white arrow.

EXAMPLE 3

Isolation and Incubation of Cartilage and Bone Marrow

Isolate a sample of cartilage tissue from the femur of an one-week old New Zealand rabbit. Remove the muscle and periosteum by microinstrument, and soak the femur in DMEM without adding fetal calf serum (FCS). Transfer the femur to a 15 ml centrifuge tube and wash twice with 10 ml phosphate buffered saline (PBS). After washing, transfer the femur to a 10 cm-wide petri dish, following which the articular cartilage is to be isolated and cut into small pieces with sterilized tissue scissor under larminar flow condition. Sift the cartilage tissue fragments through a sieve having 20 to 40 meshes to obtain cartilage tissue fragments with diameters ranging from 560 to 800 $\mu$m. Collect the cartilage tissue fragments in a 15 ml centrifuge tube and wash the tissues three times with 10 ml PBS, after which the PBS is carefully removed as clear as possible. Then, treat the cartilage tissue fragments with 5 ml collagenase in 1 mg/ml PBS and incubate in an incubator at 37° C. for 2 hours to dissociate partial chondrocytes from the cartilage surface. Treat the remained cartilage tissue fragments again with collagenase and then centrifuge at 1500 rpm for 5 minutes to separate collagenase from cartilage tissue fragments. After centrifugation, decant the clear collagenase supernatant; wash the remaining fragments and cell pellets twice with PBS and then centrifuge twice to completely remove the collegenase.

Take bone marrow cells from the pelvic cavity of a New Zealand rabbit weighted 2 kg by methods such as using 18G needle and sterile syringe to suck out 3 ml of bone marrow and mixing the bone marrow with anti-coagulant under larminar flow condition. Transfer the bone marrow to a 10-cm petri dish and add 6 ml of DMEM supplemented with fetal bovine serum into the petri dish. After a-day of incubation, remove the unattached cells and erythrocytes and change the old medium with a fresh one. Refresh the medium for every three days. Finally, allow the cells to be grown until the dish is full, at which time portions are to be placed into another dish to continue further cultivation until desired number of cells is obtained.

EXAMPLE 4

Cultivation of Multi-Layer Tissue and Cell

Inject 0.05 g of cartilage tissue blocks and cells into the hallow cavity of each multi-layered carrier using a 5 c.c. sterile syringe with 18G needle to seed each carrier with $10^6$ bone marrow stem cells. The cell volume added is 500 $\mu$l and the carriers are to be placed in a petri dish, incubated at a humid, static incubator at 37° C. for 6 hours to let the cells become attached. Next, place the carriers within a sterilized stainless steel basket and hang it in a 500 ml spinner flask to incubate. The incubation is performed in a 5% $CO_2$ incubator at 37° C., with regular replacement of fresh medium. After incubation for a period of time, take each carrier, at different points of time, away from the incubator, followed by washing with PBS, fixing in PBS solution containing 4% formalin, sectioning with the paraffin-embedded section method, and finally, staining with hematoxylin-eosin.

Figure 3:
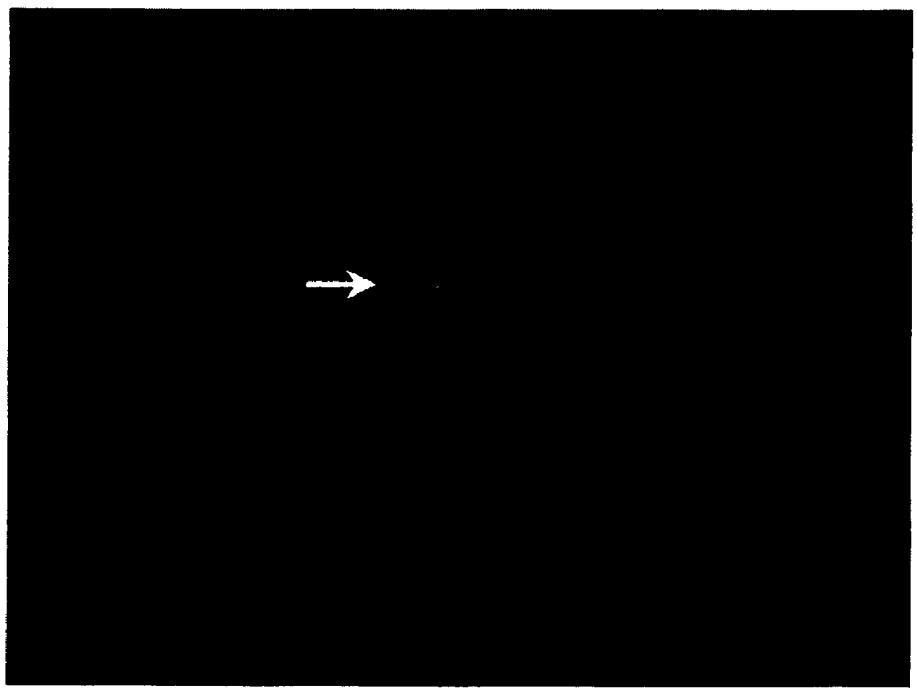
FIG. 3 shows the appearance of porous multi-layer carrier of the present invention after 4-week incubation.

Results:

FIG. 3 shows the appearance of porous multi-layer carrier of the present invention after 4-week incubation. The carrier displays intact structure after one-month incubation in culture medium. An interface between two different layers is observed at the upper edge of the carrier as indicated by the arrow.

Figure 4:
FIG. 4 shows a histological examination of a tissue after 2-week incubation at the hollow cavity by method of the present invention.

FIG. 4 shows a histological examination of tissue block after 2-week incubation inside of the hollow cavity. The newborn cartilage tissue is observed to grow around the seeded tissue blocks as indicated by arrow. The newborn cartilage tissue cells show more circular in shape than the seeded ones, and are surrounded by extracellular matrix. The newborn cartilage tissues appear to fuse with the seeded tissue blocks and grow toward the PLGA/HAP porous structure.

Figure 5:
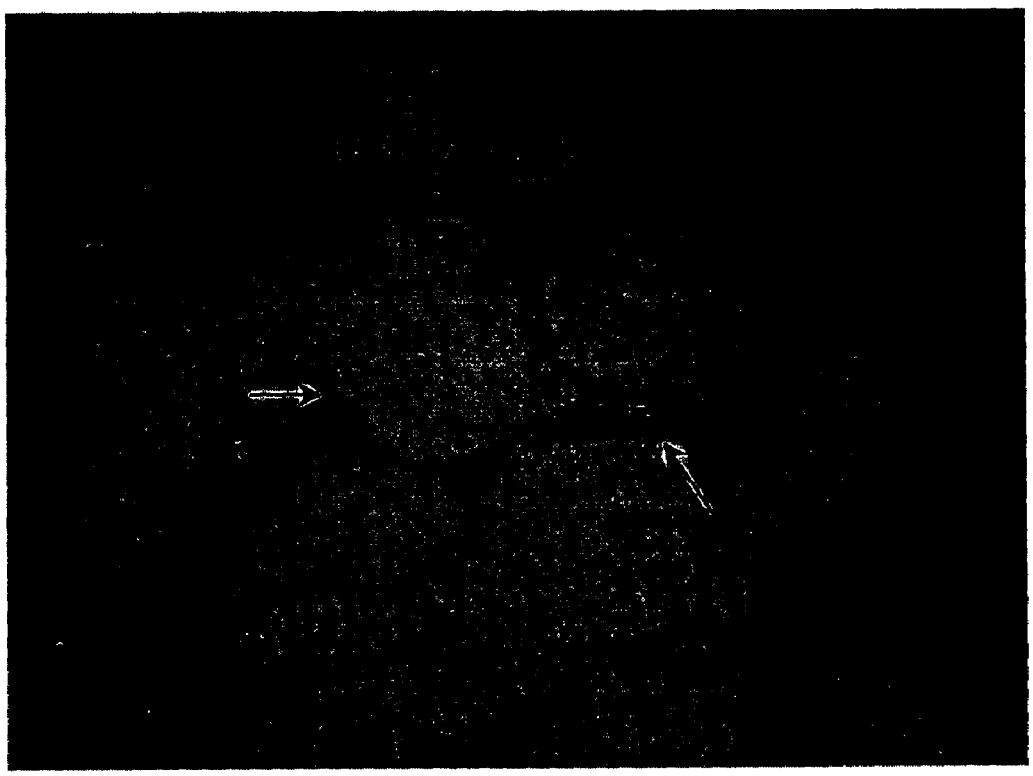
FIG. 5 shows a histological examination after seeding and 2-week incubation of bone marrow mesenchymal cells at the homogenous PLGA/HAP porous structure.

FIG. 5 shows a histological examination of bone marrow mesenchymal cells after 2-week incubation at homogenous PLGA/HAP porous structure. A layer of bone marrow mesenchymal cells can be observed at the inner side of the porous structure (indicated by arrow).

Figure 6A:
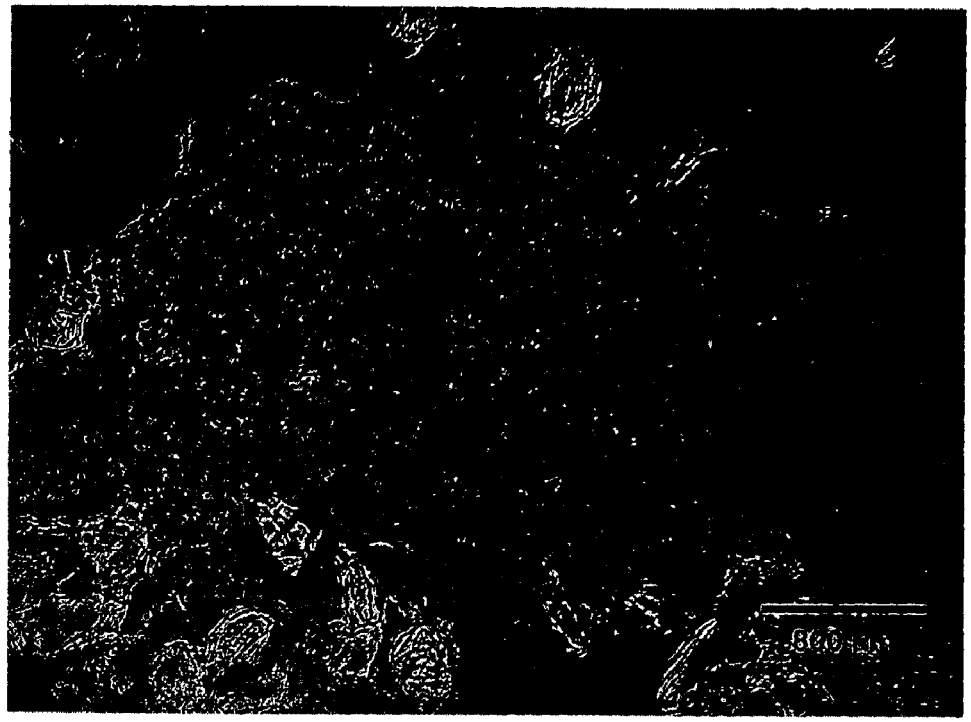
FIG. 6(a) shows a histological examination of a tissue after 4-week incubation by method of the present invention.
Figure 6B:
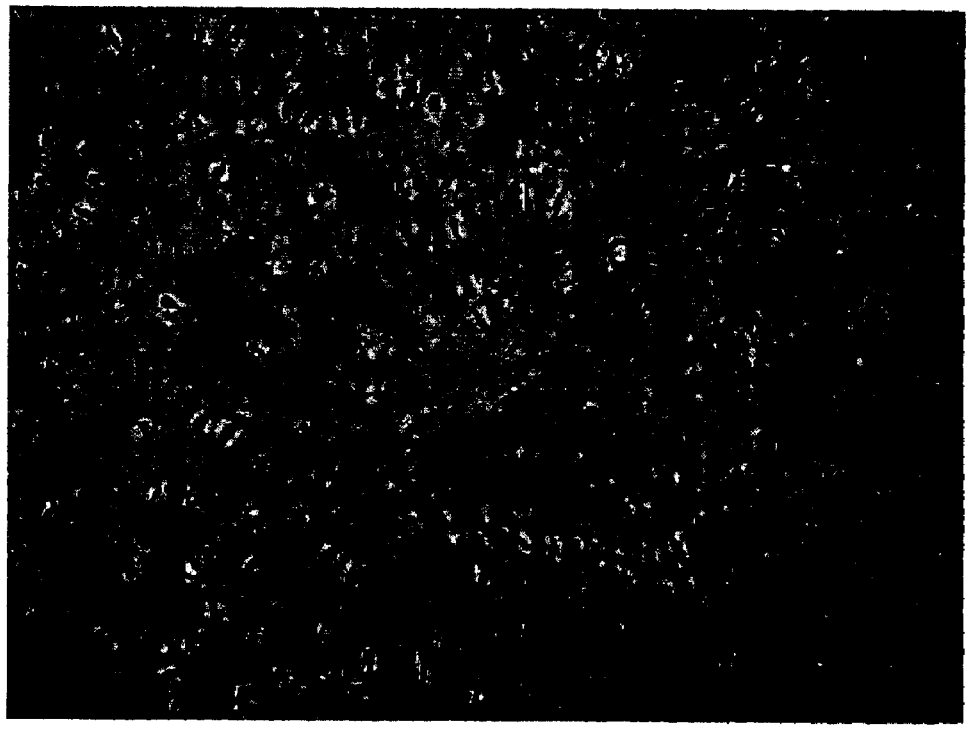
FIG. 6(b) shows a histological examination of a tissue after 4-week incubation by method of the present invention (200 times magnification).

FIG. 6(a) shows a histological examination of a tissue after 4-week incubation using culturing methods in the present invention. The newborn cartilage tissue has already fused together with seeded tissue blocks, with the size of the whole tissue block being 5.2 mm in width and 1.8 mm in depth. The underside of tissue block has grown from upper hollow cavity into the lower PLGA/HAP porous structure, forming an interface similar to that formed between cartilage and subchondral bone. FIG. 6(b) shows a histological examination, at a higher magnification, on the inner part of cartilage tissue. The newborn chondrocytes are embedded in lacunae and grown to a rather high density and can be utilized as a homologous cell line for further proliferation of a cartilage tissue.

Figure 7:
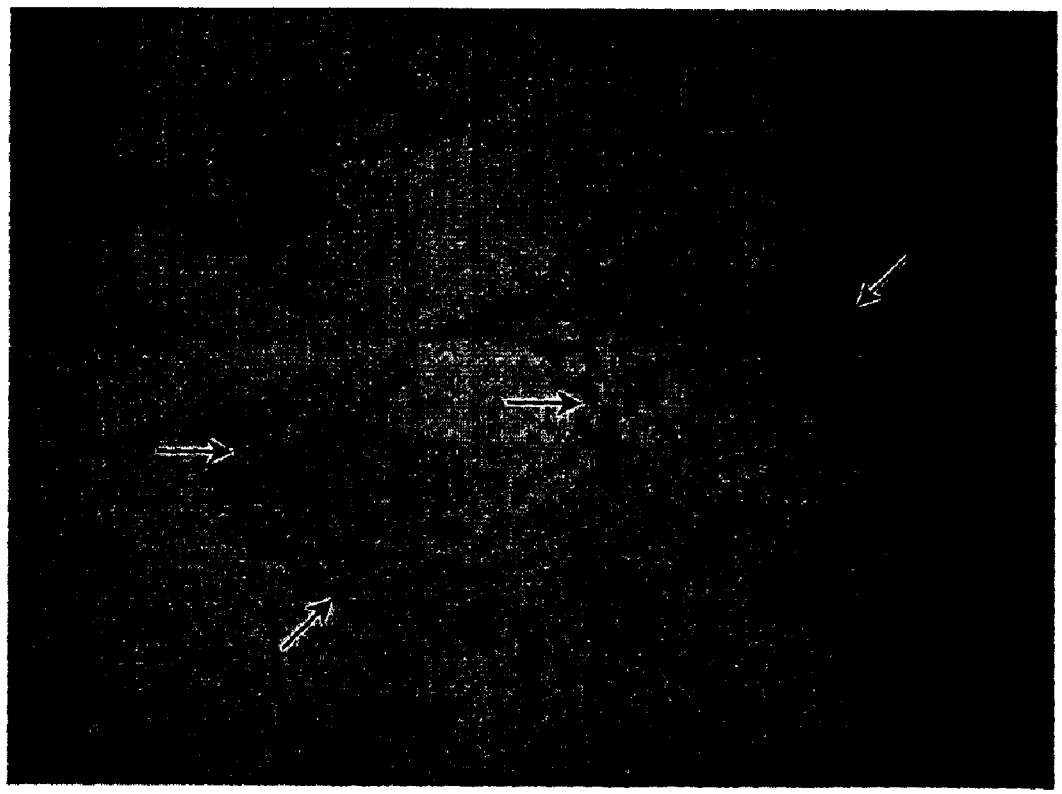
FIG. 7 shows a histological examination of a tissue after 4-week incubation at the porous structure on the lower end of the carrier by method of the present invention.

FIG. 7 shows a histological examination of a tissue after 4-week incubation at porous structure on the lower end of carrier. The pores of porous structure are filled up with the proliferated bone marrow mesenchymal cells (indicated by the arrow). No cartilage tissues are observed, indicating that, by performing methods of the present invention, various types of tissues can be cultured separately and reconstructed in vitro by taking advantage of their disparity in volume and the materials of the carrier.

The multi-layer porous carrier of the present invention can be utilized to culture multi-layer tissue. In the future, by taking only few amounts of cartilage tissue and bone marrow from patient, and incubating subsequently with the invented multi-layer porous carrier, one is able to grow large amounts of tissues that can be used as implants in transplantation surgery to treat the wide damaged area and full thickness defect.

Although the present invention has been described in considerable detail with reference to certain preferred embodiments thereof, those skilled in the art can easily understand that all kinds of alterations and changes can be made within the spirit and scope of the appended claims. Therefore, the spirit and scope of the appended claims should not be limited to the description of the preferred embodiments contained herein.

What is claimed is:

1. A method for multi-layer tissue culturing in vitro, comprising:
   providing a porous multi-layer carrier having a hollow cavity;
   placing tissue blocks within said hollow cavity of said carrier;
   seeding cells into said carrier; and
   incubating said tissue blocks and cells within said carrier in a culture medium.

2. The method according to claim 1, wherein the diameters of said tissue blocks are larger than the pore diameters of said porous multi-layer carrier.

3. The method according to claim 1, wherein the pore diameter of said multi-layer porous carrier ranges from 50 to 500 μm.

4. The method according to claim 1, wherein the diameter of said tissue blocks ranges from 500 to 1000 μm.

5. The method according to claim 1, wherein said tissue blocks are granulated carriers attached with cells or cell aggregates.

6. The method according to claim 1, wherein said multi-layer porous carrier is made of bioabsorbable polymer material.

7. The method according to claim 6, wherein said bioabsorbable polymer materials are selected from the group consisting of polyglycolic acid (PGA), polylactic acid (PLA), poly (lactic-co-glycolic) acid (PLGA), polyanhydride, polycapralactone (PCL), polydioxanone and polyorthoester.

8. The method according to claim 1, wherein said carrier is a composite material including an absorbable polymer material.

9. The method according to claim 8, wherein said composite material includes other materials selected from the group consisting of: hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), calcium pyrophosphate (CPP), collagen, gelatin, hyaluronic acid, chitin, and poly(ethylene glycol).

10. A multi-layered porous carrier, which comprises:
    a hollow cavity for receiving tissue blocks, wherein said hollow cavity is surrounded by a wall of porous substrate; and
    a porous structure, which is located under said hollow cavity and provided for cell attachment.

11. The multi-layer porous carrier according to claim 10, wherein the diameter of said tissue blocks ranges from 500 to 1000 μm.

12. The multi-layer porous carrier according to claim 10, wherein the pore diameter of said multi-layer porous carrier ranges from 50 to 500 μm.

13. The multi-layer porous carrier according to claim 10, wherein said multi-layer porous carrier is made of a bioabsorbable polymer material.

14. The multi-layer porous carrier according to claim 13, wherein said bioabsorbable polymer materials are selected from the group consisting of polyglycolic acid (PGA), polylactic acid (PLA), poly (lactic-co-glycolic) acid (PLGA), polyanhydride, polycapralactone (PCL), polydioxanone and polyorthoester.

15. The multi-layer porous carrier according to claim 10, wherein said multi-layer porous carrier is made of a composite material including a bioabsorbable polymer material.

16. The multi-layer porous carrier according to claim 15, wherein said composite material including other materials selected from the group consisting of: hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), calcium pyrophosphate (CPP), collagen, gelatin, hyaluronic acid, chitin, and poly(ethylene glycol).

17. A multi-layer implant fabricated by using the method of claim 1, comprising steps of:
    providing a porous multi-layered carrier having a hollow cavity;
    placing tissue blocks within said hollow cavity of said carrier;
    seeding cells into said carrier; and
    incubating said tissue blocks and cells within said carrier in a culture medium.

18. The multi-layer implant according to claim 17, wherein said implant is bone implant.

19. The method according to claim 17, wherein said cell is a preparation of living tissue including primary tissue explants and preparations thereof, an isolated cell and a cell line.

* * * * *